(12) United States Patent
Boernert et al.

(10) Patent No.: US 9,600,912 B2
(45) Date of Patent: Mar. 21, 2017

(54) SPATIALLY CORRECTED NUCLEAR IMAGE RECONSTRUCTION

(71) Applicant: KONINKLIJKE PHILIPS N.V., Eindhoven (NL)

(72) Inventors: Peter Boernert, Hamburg (DE); Steffen Renisch, Hamburg (DE); Susanne Heinzer, Bern (CH)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

(21) Appl. No.: 14/376,863

(22) PCT Filed: Feb. 15, 2013

(86) PCT No.: PCT/IB2013/051222
§ 371 (c)(1),
(2) Date: Aug. 6, 2014

(87) PCT Pub. No.: WO2013/121379
PCT Pub. Date: Aug. 22, 2013

(65) Prior Publication Data
US 2015/0003709 A1    Jan. 1, 2015

Related U.S. Application Data (60) Provisional application No. 61/599,563, filed on Feb. 16, 2012, provisional application No. 61/604,089, filed on Feb. 28, 2012.

(51) Int. Cl.
*G06K 9/00* (2006.01)
*G06T 11/00* (2006.01)
*A61B 6/03* (2006.01)
*A61B 5/055* (2006.01)
*A61B 6/00* (2006.01)

(52) U.S. Cl.
CPC ............ *G06T 11/005* (2013.01); *A61B 5/055* (2013.01); *A61B 6/032* (2013.01); *A61B 6/037* (2013.01);
(Continued)

(58) Field of Classification Search
CPC ..... G06T 11/005; G06T 11/006; A61B 5/055; A61B 6/032; A61B 6/037; A61B 6/463;
(Continued)

(56) References Cited

U.S. PATENT DOCUMENTS

2010/0278406 A1    11/2010    Delso et al.
2011/0164801 A1    7/2011    Gagnon et al.

OTHER PUBLICATIONS

Fukuchi, Kazuki, et al. "Attenuation correction for cardiac dual-head camera coincidence imaging using segmented myocardial perfusion SPECT." J Nucl Med 41 (2000): 919-925.*

(Continued)

*Primary Examiner* — Nirav G Patel (57) ABSTRACT

A medical imaging system (5) includes one or more processors and a display device (36). The one or more processors are programmed to receive (60) a first image (10) contrasting regions of tissue with a distinct radiotracer accumulation probability and generate (64) a constraint map (20) based on the regions of tissue with the distinct radiotracer accumulation probability. The one or more processors are programmed to reconstruct (70) a second image (44) with redistribution of a measured radiotracer based on the constraint map (20) and acquired image raw data (23) registered to the constraint map. The display device (36) displays the reconstructed second image.

19 Claims, 5 Drawing Sheets

(52) U.S. Cl.
CPC ............ *A61B 6/463* (2013.01); *A61B 6/5205* (2013.01); *G06T 11/006* (2013.01); *A61B 6/466* (2013.01); *A61B 6/5247* (2013.01); *A61B 6/563* (2013.01)

(58) Field of Classification Search
CPC ..... A61B 6/466; A61B 6/5205; A61B 6/5247; A61B 6/563
See application file for complete search history.

(56) References Cited

OTHER PUBLICATIONS

Baete, K., et al.; Evaluation of anatomy based reconstruction for partial volume correction in brain FDG-PET; 2004; NeuroImage; 23:305-317.

Genchellac, H., et al.; Computed Tomographic and Magnetic Resonance Imaging Findings of Asymptomatic Intra-Abdominal Gastrointestinal System Lipomas; 2008; Journal of Computer Assisted Tomography; 32(6)841-847.

Hofmann, M., et al.; MRI-Based Attenuation Correction for Whole-Body PET/MRI: Quantitative Evaluation of Segmentation-and Atlas-Based Methods; 2011; The Journal of Nuclear Medicine; 52(9)1392-1399.

Rousset, O. G., et al.; Correction for Partial Volume Effects in PET: Principle and Validation; 1998; The Journal of Nuclear Medicine; 39(5)904-911.

Soret, M., et al.; Partial-Volume Effect in PET Tumor Imaging; 2007; The Journal of Nuclear Medicine; 48(6)932-945.

Valls, C., et al.; Fat in the Liver: diagnosis and characterization; 2006; European Radiology; 16(10)2292-2308.

* cited by examiner

SPATIALLY CORRECTED NUCLEAR IMAGE RECONSTRUCTION

CROSS REFERENCE TO RELATED APPLICATIONS

This application is a national filing of PCT application Serial No. PCT/IB2013/051222, filed Feb. 15, 2013, published as WO 2013/121379 A2 on Aug. 22, 2013, which claims the benefit of U.S. provisional application Ser. No. 61/599,563 filed Feb. 16, 2012 and U.S. provisional application Ser. No. 61/604,089 filed Feb. 28, 2012, both of which are incorporated herein by reference.

The following relates generally to medical imaging. It finds particular application in conjunction with image reconstruction of nuclear imaging data, and will be described with particular reference thereto. However, it will be understood that it also finds application in other usage scenarios and is not necessarily limited to the aforementioned application.

In nuclear medicine, reconstruction uses measured gamma event data to reconstruct the spatial distribution of a radiotracer. The spatial distribution of an accumulated radiotracer is used to e.g. detect tumors and other suspicious lesions. The estimated spatial distribution of detected tumors is used to measure or stage the detected tumors. However, the spatial resolution of nuclear medicine imaging is limited, also due to the underlying physics, in comparison with higher resolution imaging techniques such as magnetic resonance (MR) or x-ray computed tomography (CT). The nuclear medicine data is used to calculate a standardized uptake value (SUV) which is based on a volume and the amount of radiotracer present in that volume. However, the limited resolution of the nuclear medicine affects the accuracy of volume measured and the amount of radiotracer present in a volume. Typically, the SUV accuracy is limited. For example, small lesions are often underestimated due to limited spatial resolution.

Typically, a volume is measured based on the resolution of the device used to record the gamma event data. Efforts to improve the resolution include time of flight positron emission tomography (TOF-PET) and the like. However, in some cases tissue is present in regions which record gamma events such as fatty tissue which rarely accumulates the radiotracer. However, the volume of radiotracer measured to calculate the SUV includes the volume of such tissue even though the tissue may in actuality not accumulate the tracer. Including the tissue not accumulating the tracer increases the total volume while decreasing the density of the radiotracer over that volume. Radiotracer SUV for a small lesion is typically spread over a larger volume which underestimates the accumulation of the tracer.

Nuclear imaging is designed to measure metabolic activity while anatomical imaging is designed for high spatial resolution for differentiation of anatomical tissues.

The following discloses a new and improved spatially corrected nuclear image reconstruction which addresses the above referenced matters, and others.

In accordance with one aspect, a medical imaging system includes one or more processors and a display device. The one or more processors are programmed to receive a first image contrasting regions of tissue with a distinct radiotracer accumulation probability and generate a constraint map based on the regions of tissue with the distinct radiotracer accumulation probability. The one or more processors are programmed to reconstruct a second image with redistribution of a measured radiotracer based on the constraint map and acquired image raw data registered to the constraint map. The display device displays the reconstructed second image.

In accordance with another aspect, a method includes receiving a first image contrasting regions of tissue with a distinct radiotracer accumulation probability and generating a constraint map based on the regions of tissue with the distinct radiotracer accumulation probability. Image raw data generated by a nuclear imaging device is acquired and includes a measured radiotracer. A second image based on the acquired image data and the constraint map is reconstructed. The reconstructed second image is displayed on a display device.

In accordance with another aspect, an imaging system includes a redistributor. The redistributor reconstructs an image including redistribution of a measured radiotracer based on a constraint map which identifies regions of tissue to be excluded and an acquired image raw data from a nuclear imaging device.

One advantage is exclusion of regions in reconstruction known to accumulate radiotracers only marginally.

Another advantage resides in atlas based confidence measures for restrictions of radiotracer distribution.

Another advantage resides in more accurate estimation of tumor SUV values.

Still further advantages will be appreciated to those of ordinary skill in the art upon reading and understanding the following detailed description.

The invention may take form in various components and arrangements of components, and in various steps and arrangement of steps. The drawings are only for purposes of illustrating the preferred embodiments and are not to be construed as limiting the invention.

Figure 1:
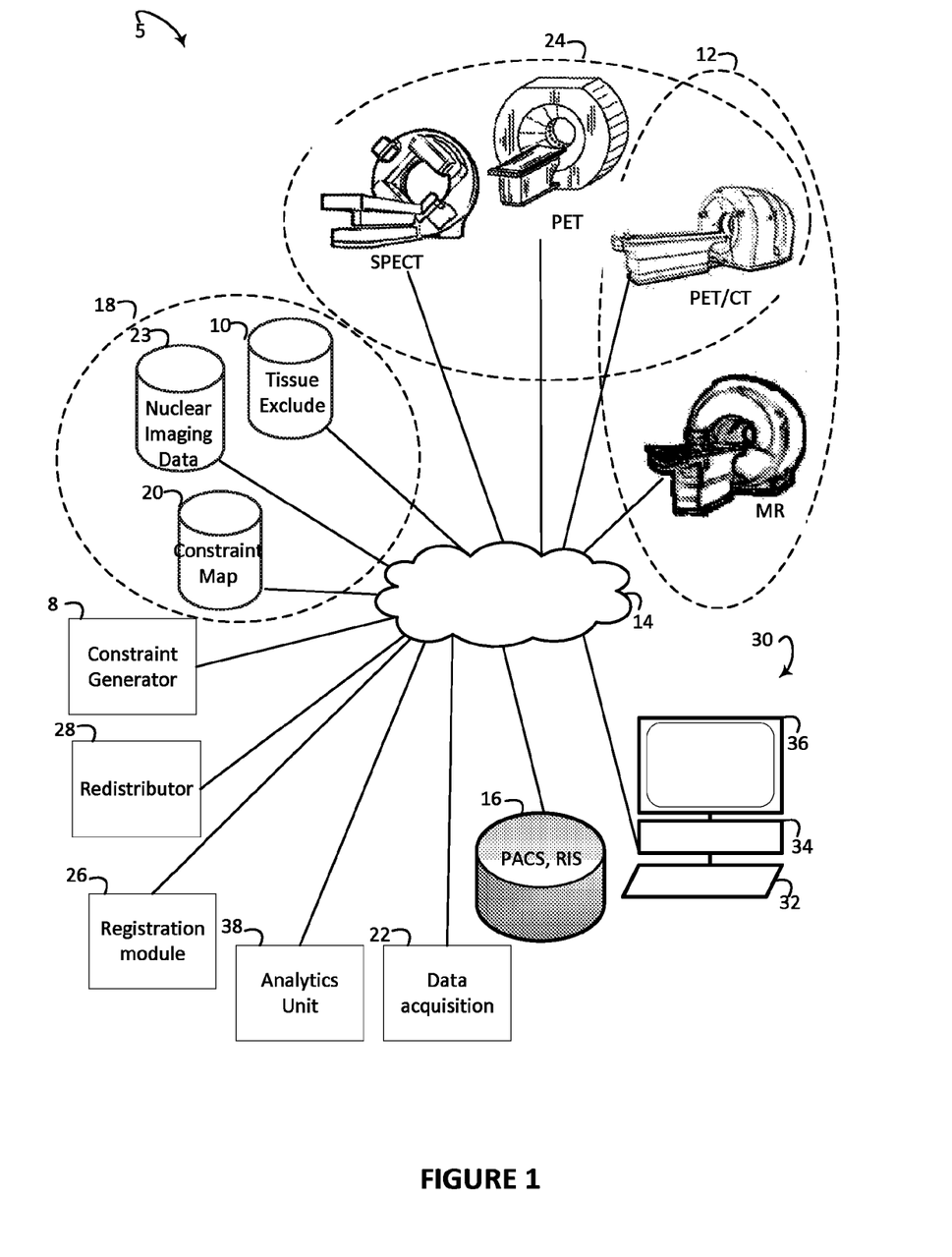
FIG. 1 schematically illustrates an embodiment of the augmented nuclear medicine reconstruction system.

With reference to FIG. 1, an embodiment of the medical imaging system 5 is schematically illustrated. A constraint generator 8 receives an image 10 contrasting regions of tissue to be excluded. The image can be received directly from an anatomical imaging device 12 such as magnetic resonance (MR), x-ray computed tomography (CT), and the like or indirectly via a network 14. The network 14 can be wired or wireless, direct or indirect, private or public such as the Internet, or any combination. For example, an image contrasting fatty tissue uses a whole body Dixon scan, an MR scan that is able to separate the water and fat body distribution, with an isotropic spatial resolution of 3×3×3 mm$^3$ is obtained directly from a MR device. In another example, a CT scan based on Hounsfield units distinguishes between water, fat, and bone. The image can also be received from a storage management system 16 such as a Picture Archiving and Communication System (PACS), a Radiology Information System (RIS), and the like, or a data store 18 such as local memory, disk, network attached storage and the like. The constraint generator 8 uses the tissues contrasted in the image 10 to generate a constraint map 20. The constraint map 20 can be stored in a data store.

A data acquisition module 22 acquires imaging data 23 from a nuclear imaging device 24 such as Positron Emission Tomography (PET), Single Photon Emission Computed Tomography (SPECT), and the like. The imaging data includes information about each recorded gamma event, or cumulative information thereof (counts). The radioactivity of the tracer can be partially reconstructed as a volume of voxels and each voxel represented as a total for a period, a mean, a maximum, and the like.

A registration module 26 registers the volume of acquired imaging data 23 and the generated constraint map 20. Note that on some systems (e.g. designated PET/CT and PET/MR combination systems) this registration might be accomplished by hardware. The constraint map is obtained directly from the constraint generator 8 via the network 14, or indirectly through the data store 18. The registration can in addition register the image 10 and other information such as an anatomical atlas, to provide additional information for the constraint map. The registered image and other information provide anatomical information about the tissue types and the tissue type form and function. The anatomical atlas is typically stored in the storage management system 16, but can be stored in a separate data store 18.

Using one or more processors programmed, a redistributor 28 reconstructs a second image based on the acquired imaging raw data 23 and the constraint map 20. The redistributor 28 redistributes the voxels of measured radiotracer based on the constraint map 20. This information is used in the subsequent reconstruction of the nuclear imaging data. Using the additional constraints given in the constraint map, the inverse problem reconstructing the corresponding nuclear image is solved. The redistribution improves the accuracy of the radiotracer SUV and the quantification of the radiotracer density. The improvement in accuracy of the radiotracer SUV and the quantification of the radiotracer density increases the accuracy of tumor staging.

A workstation 30 connects to the network 14 and a healthcare practitioner selects the image 10 using at least one input device 32 connected to the workstation 30. The workstation 30 includes an electronic processor or electronic processing device 34, a display 36 which displays the image, menus, panels, and user controls, and the at least one input device 32 which inputs the healthcare practitioner selections. The workstation 28 can be a desktop computer, a laptop, a tablet, a mobile computing device, a smartphone, and the like. The input device 32 can be a keyboard, a mouse, a microphone, and the like.

An analytics unit 38 calculates volumetric and other data based on the reconstructed image. The analytics unit 38 can calculate various statistics using the reconstructed image such as the mean SUV, maximum SUV, and the like for each voxel, region, total volume, etc. The display device 36 can display the volumetric data with the reconstructed image or separately. The display device 36 can overlay the first image and the reconstructed image for spatial comparisons by the healthcare practitioner.

The constraint generator 8, data acquisition module 24, registration module 26, analytics unit 38, and redistributor 28 are suitably embodied by an electronic data processing device, such as the electronic processor or electronic processing device of the workstation 28, or by a network-based server computer operatively connected with the workstation by the network, or so forth. Moreover, the disclosed constraint map generation, tissue identification techniques, and image reconstruction are suitably implemented as a non-transitory storage medium storing instructions (e.g., software) readable by an electronic data processing device and executable by the electronic data processing device to perform the disclosed data acquisition, registration, image reconstruction, map generation and tissue identification techniques.

Figure 2:
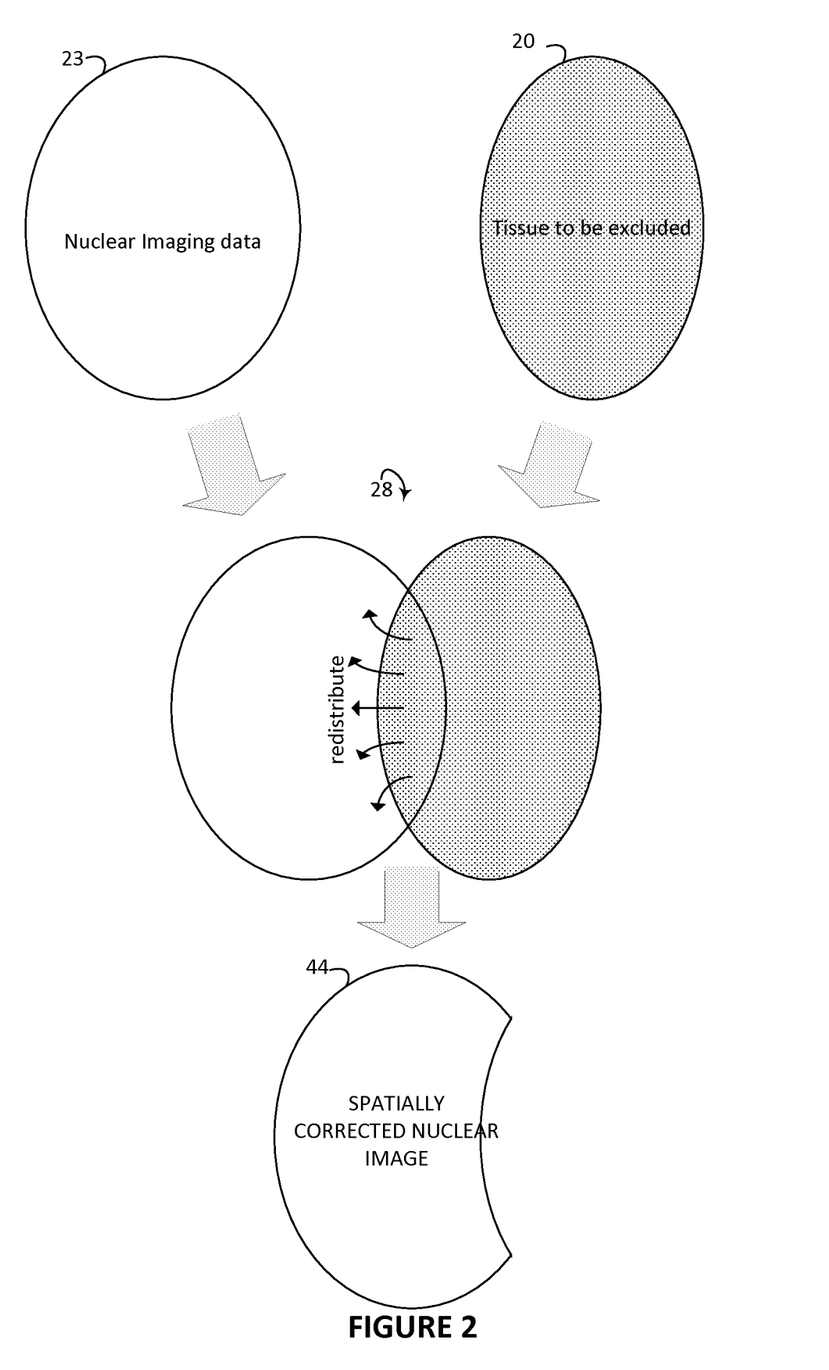
FIG. 2 diagrammatically illustrates an example of using an constraint map to spatially correct a volume in a nuclear medicine image.

In FIG. 2, an example of using an constraint map to spatially correct a volume in a nuclear medicine image is diagrammatically illustrated. A first image is received which contrasts regions with different probabilities for tracer accumulation. The first image provides detailed resolution of the regions with different tracer accumulation probabilities. In this example, only one region with probability 0 (i.e. no tracer accumulation) is shown, but more regions are contemplated, and additional contrasts are also contemplated. For example, multiple tissue types can be contrasted in a single image or between images. If tissue types are identified and correlated as not supporting tumors or not accumulating the radiotracer, then the regions of identified tissue are excluded by assigning zero or low probability values. Generally, an image depicting a physical or chemical property of a tissue with a high spatial resolution that affects the contrast mechanism can be used. A constraint map 20 is generated which identifies the region of tissue to be excluded which in this example is the one region of the first image. This constraint map could be understood in its simplest implementation as binary information in the sense, that the nuclear event might stem from this region (i.e. accumulation probability 100%) or not (i.e. accumulation probability 0). In a more general sense this map should be understood as a measure for the probability that an event originates from a certain spot. The use of a probability measure is helpful e.g. to accommodate for partial volume effects, which means that several tissue types can occupy a measured voxel to a certain percentage.

Imaging data 23 is acquired which includes a radiotracer measurement. The radiotracer correlates e.g. with vital tumor tissue or lesions. However, the radiotracer measurement from the acquired data provides limited resolution. The imaging data is registered with the constraint map which shows the overlap between the measured radiotracer from the imaging data and the excluded regions identified in the constraint map 20.

The redistributor or redistribution process 28 uses the constraint map 20 and one or more redistribution functions to redistribute the voxels of measured radiotracer excluded by the constraint map. The reconstruction minimizes $\|\rho - \Psi f\|$ subject to $\|P\rho - s\| < $ error threshold, where $\rho$ are the nuclear activity image projections to be reconstructed, P is a transform operator and usually includes a filtered back-projection or a similar inverse projection related to the measurement process, and $\Psi$ is an operator acting on the spatial constraint map to ensure during the minimization process that the nuclear signal distribution, the image $\rho$, preferably originates from regions which are less constrained. So the image reconstruction can be related to the constraint, e.g. the distribution of fat described by f. Other minimizations are possible such as $\|\Psi'(\rho - f)\|$ and $\|\rho - \Psi''' w\|$ where w is in this example the water information. A resulting reconstructed second image 44 is shown with the voxels redistributed and the second image reconstructed with spatial correction. With the spatially corrected volume represented as the second image, a more accurate SUV is calculated.

Very briefly summarized, a nuclear image and a high resolution anatomical image of the same region are generated and registered. In one conceptualization, each low resolution nuclear voxel is subdivided into smaller high resolution voxels, each corresponding to a high resolution voxel of the anatomical image. Initially all of the high resolution voxels into which one of the low resolution voxels was subdivided have the same value. For each high resolution voxel of the nuclear image, a processor looks to the corresponding high resolution voxel of the anatomical image to identify the tissue type. If the tissue type is one that does not take up the radioactive tracer, then the radiation attributed to the high resolution voxel of the nuclear image is redistributed to the other high resolution voxels of the same low resolution nuclear image voxel. This redistribution is realized preferably by a new reconstruction of the nuclear image raw data including appropriate constraints. In this manner, the radiation uptake for each large, low resolution nuclear voxel is reassigned only to the smaller high resolution voxels which contain tissue that would uptake the radiotracer, thereby improving the resolution of the nuclear image higher than the inherent capability of the nuclear images.

Figure 3A:
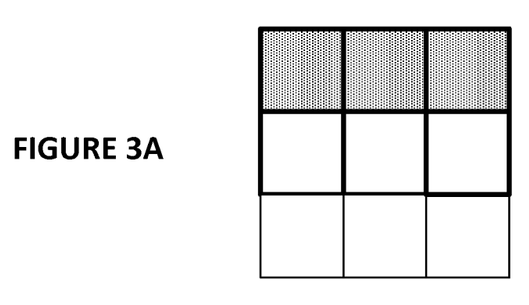
FIGS. 3A and 3B illustrate one example of how a constraint map redistributes measured radiotracer.
Figure 3B:
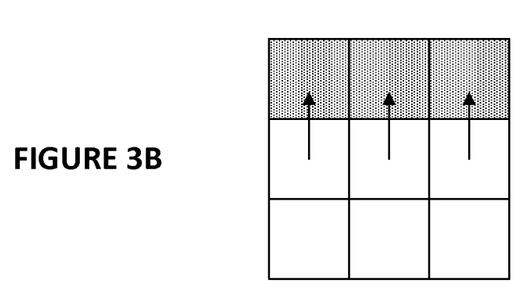

In FIGS. 3A-3B, one example of how a constraint map used in an appropriate reconstruction process redistributes measured radiotracer is illustrated. FIG. 3A shows a volume of voxels. Unshaded voxels are voxels identified by the constraint map as regions to be excluded. Voxels with dark borders illustrate voxels which record measurements of radiotracer such as gamma events count totals or statistics such as mean, max, etc. over time.

In the example shown in FIG. 3B, the redistribution function is the movement of the counts from voxels identified by the constraint map to the nearest neighbor not excluded by the constraint map. In the example, this is a point to point redistribution. The radiotracer measurements of voxels in the unshaded region are moved from the unshaded region and combined with the voxels in the shaded region. For example, the counts of radiotracer in one voxel would be zeroed and the count of the nearest neighbor would be correspondingly increased. The redistribution function can include a variety of techniques such as redistribution to a group of neighboring voxels in a one to many relationship, contouring which moves bands of voxels in a many to many relationship, folding techniques, smoothing, etc. The function includes distance and concentration of radiotracer as factors in the redistribution.

Figure 4:
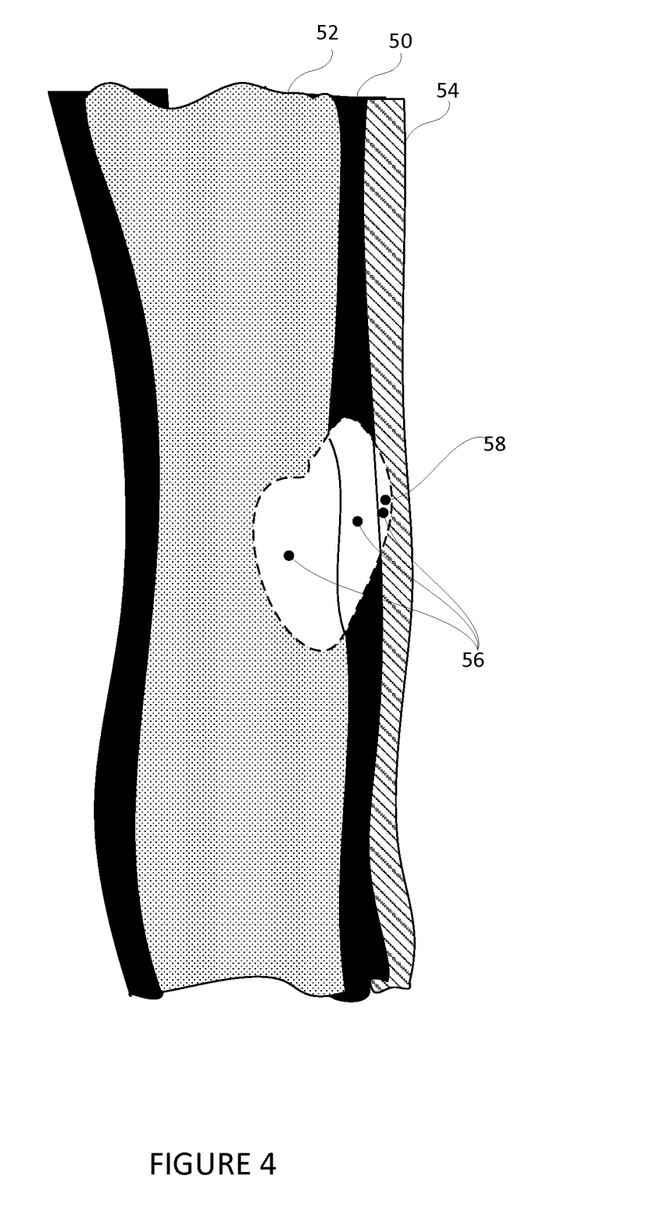
FIG. 4 diagrammatically illustrates an example of modifying the constraint map for different tissue types.

With reference to FIG. 4, diagrammatically illustrated is an example of modifying the constraint map for different tissue types. The diagram shows a sagittal section of bone including bone 50, bone marrow 52 and fatty tissue 54. The bone marrow also includes fatty tissue but may accumulate the radiotracer. In this example, anatomical information is used to modify the constraint map. The anatomical information can be included from an atlas or other source. For example, bone locations which can include possible bone metastases are included. In cases of liposarcomas or atherosclerotic plaque additional or other a-priori information is used from such sources as the patient medical record. The anatomical information is used to modify the constraint map. For example, fatty tissue included in the bone marrow is not excluded in the constraint map while fatty tissue outside the bone is excluded. In addition to the regions contrasted in the first image, anatomical information can be used to modify or refine the final constraint map.

Other information of potential suspect tissue could be incorporated in the constraint map. For example, the information about infected lymph nodes obtained from diffusion weighted MRI are used to calculate a nuclear event distribution under the assumption that suspect tissue is involved. Such information could be helpful for the physician to test different clinical hypotheses based on the measured data. The constraint map can include organs known to accumulate radiotracer. For organs which accumulate the radiotracer, the redistribution function can exclude or downweight regions with a distribution function such as a null redistribution of the measured radiotracer to effectively mask the organ enriched radiotracer. The region 56 shown in white represents the uncorrected region of radiotracer.

The constraint map, in this example, includes the region diagonally shaded fatty tissue 54. The black region 50 illustrates the bone and the shaded region 52 illustrates bone marrow. The bone and the bone marrow are not included in the constraint map. During reconstruction of the second image 44, the redistribution function redistributes the measured radiotracer only in the region indicated in the constraint map which in this instance includes the area marked 58. The anatomic information can also be displayed with the reconstructed image to provide confidence based measures and spatial relationships.

Figure 5:
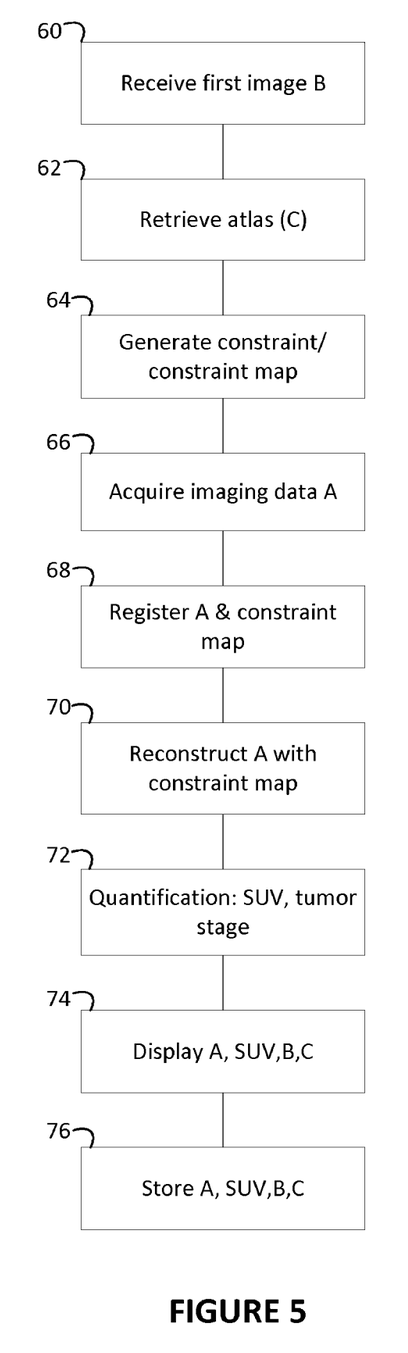
FIG. 5 flowcharts one method of using the system to reconstruct a spatially corrected nuclear medicine image.

In FIG. 5 one method is flowcharted of using the system to reconstruct a high resolution nuclear medicine image with spatial correction. In a step 60, the first image is received which contrasts regions of tissue to be excluded. The first image can be received directly from the imaging device or indirectly received from storage. The contrasted regions of tissue to be excluded can be a range and include a single tissue or tissue characteristic or multiple tissue types. In an optional step 62, an anatomical atlas is retrieved and co-registered with the first image. The anatomical atlas provides information which can be used to modify regions of tissue to be excluded.

In a step 64, the constraint generator generates the constraint map 20 based on the regions of contrasted tissue to be excluded from the first image and optionally modified by the anatomical atlas or other information. The constraint map identifies regions to be excluded of measured radiotracer.

Imaging data is acquired in a step 66 by the data acquisition module, and the imaging data includes the measured radiotracer. The measured radiotracer can be raw event counts or statistics derived from the raw event counts such as mean, maximum and the like. The imaging data can be acquired directly from the imaging device such as a PET scanner, SPECT scanner, hybrid or combination MR/PET, CT/PET, CT/SPECT, and the like. The imaging data can be received from storage memory which holds previously acquired imaging data. The constraint map and the acquired imaging data are registered by the registration module 26 in an optional step 68. The registration provides a spatial mapping or transform between the constraint map and the acquired imaging data. Some systems are designed to be inherently registered and therefore do not need a registration step.

In a step 70, the redistributor 28 reconstructs the second image 44 and redistributes the measured radiotracer based on the acquired imaging data and the constraint map. The redistributor includes one or more functions which redistribute the constrained regions of tissue. The measured radiotracer in the spatially corrected volume can optionally be processed by the analytics unit 38 in a step 72. The analytics unit can quantify SUVs based on various volumetric measurements using the reconstructed volume and measured radiotracer. The analytics unit can optionally in a step 72, provide an estimate of the tumor stage. In a step 74, the reconstructed image is displayed by the display device. The second image can be overlayed with the received first image, atlas information, analytics unit quantified measurements, etc. In a step 76, the second image and/or other information can be stored in a storage management system such as a PACS, RIS, etc.

It is to be appreciated that in connection with the particular illustrative embodiments presented herein certain structural and/or function features are described as being incorporated in defined elements and/or components. However, it is contemplated that these features may, to the same or similar benefit, also likewise be incorporated in other elements and/or components where appropriate. It is also to be appreciated that different aspects of the exemplary embodiments may be selectively employed as appropriate to achieve other alternate embodiments suited for desired applications, the other alternate embodiments thereby realizing the respective advantages of the aspects incorporated therein.

It is also to be appreciated that particular elements or components described herein may have their functionality suitably implemented via hardware, software, firmware or a combination thereof. Additionally, it is to be appreciated that certain elements described herein as incorporated together may under suitable circumstances be stand-alone elements or otherwise divided. Similarly, a plurality of particular functions described as being carried out by one particular element may be carried out by a plurality of distinct elements acting independently to carry out individual functions, or certain individual functions may be split-up and carried out by a plurality of distinct elements acting in concert. Alternately, some elements or components otherwise described and/or shown herein as distinct from one another may be physically or functionally combined where appropriate.

In short, the present specification has been set forth with reference to preferred embodiments. Obviously, modifications and alterations will occur to others upon reading and understanding the present specification. It is intended that the invention be construed as including all such modifications and alterations insofar as they come within the scope of the appended claims or the equivalents thereof. That is to say, it will be appreciated that various of the above-disclosed and other features and functions, or alternatives thereof, may be desirably combined into many other different systems or applications, and also that various presently unforeseen or unanticipated alternatives, modifications, variations or improvements therein may be subsequently made by those skilled in the art which are similarly intended to be encompassed by the following claims.

What is claimed is:

1. A medical imaging system, comprising:
   one or more processors programmed to:
   receive a first image contrasting regions of tissue with a distinct radiotracer accumulation probability;
   generate a constraint map based on the regions of tissue with the distinct radiotracer accumulation probability;
   receive raw image data;
   redistribute the received raw image data by subdividing a low resolution voxel of the acquired image raw data into corresponding higher resolution voxels of the first image and reassigning values of the subdivided low resolution voxel to the higher resolution first image voxels based on the constraint map; and
   reconstruct the redistributed raw image data into a second image; and
   a display device which displays the reconstructed second image.

2. The medical imaging system according to claim 1, wherein the constraint map includes a redistribution function redistributing the raw image data.

3. The medical imaging system according to claim 1, wherein the first image contrasts fatty tissue.

4. The medical imaging system according to claim 1, wherein the first image is received from at least one of:
   a magnetic resonance (MR) scanner;
   a X-ray computed tomography (CT) scanner; and
   an atlas; and
   the imaging raw data is acquired from at one of:
   positron emission tomography (PET); and
   single proton emission computed tomography (SPECT).

5. The medical imaging system according to claim 4, wherein the anatomical locations includes organs known to enrich radiotracer uptake.

6. The medical imaging system according to claim 1, wherein the processor is further programmed to:
   compare contrasted regions of tissue to an anatomical atlas;
   modify the constraint map to include contrasted regions based on anatomical location.

7. The medical imaging system according to claim 1, wherein the radiotracer measurement includes either one of a mean standard uptake value (SUV) and a maximum standard uptake value of the reconstructed second image.

8. The medical imaging system according to claim 1, wherein the one or more processors are further programmed to:
   calculate a measurement of the radiotracer based on the reconstructed second image which includes a volume of voxels of radiotracer measurements.

9. The medical imaging system according to claim 1, wherein the display device displays the calculated measurement of radiotracer volume of voxels.

10. The medical imaging system according to claim 1, wherein the display device overlays the first image.

11. A medical imaging system, comprising:
    one or more processors programmed to:
    receive a first image contrasting regions of tissue with a radiotracer accumulation probability;
    generate a constraint map based on the regions of tissue with the radiotracer accumulation probability; and
    reconstruct a second image with redistribution of a measured radiotracer based on the constraint map and acquired image raw data registered to the constraint map; and
    a display device configured to display the reconstructed second image;
    wherein the constraint map includes a redistribution function for voxels in constrained regions of tissue; and
    wherein the redistribution function includes subdividing a low resolution voxel of the acquired image raw data into corresponding higher resolution voxels of the first image and reassigning values of the subdivided low resolution voxel to the higher resolution first image voxels based on the constraint map.

12. A method, comprising:
    receiving a first image contrasting regions of tissue with a distinct radiotracer accumulation probability;
    generating a constraint map based on the regions of tissue with the distinct radiotracer accumulation probability;
    acquiring image raw data generated by a nuclear imaging device which image raw data includes radiotracer distribution data;
    subdividing a low resolution voxel of the acquired image raw data into corresponding higher resolution voxels of the first image and reassigning values of the subdivided low resolution voxel to the first image based on the constraint map;

reconstructing a second image based on the acquired image data and the constraint map; and displaying the reconstructed second image on a display device.

13. The method according to claim 12, wherein the first image contrasts fatty tissue.

14. The method according to claim 12, further including:

comparing the contrasted regions of tissue to an anatomical atlas; and modifying the constraint map to included contrasted regions based on anatomical location.

15. The method according to claim 14, wherein the anatomical location is bone marrow.

16. The method according to claim 12, further including:

calculating an image of the radiotracer distribution based on the reconstructed second image which includes a volume of voxels of radiotracer measurements.

17. A non-transitory computer-readable medium carrying software which controls one or more processors to perform the method of claim 12.

18. A system comprising:

one or more processors programmed to perform the method according to claim 12.

19. An imaging system, comprising:

a redistributor which reconstructs an image including redistributing of a measured radiotracer based on a constraint map which identifies regions of tissue to be excluded and an acquired image raw data from a nuclear imaging device, wherein the constraint map includes a redistribution function configured to:

subdivide a low resolution voxel of the acquired image raw data into corresponding higher resolution voxels of the first image and reassign values of the subdivided low resolution voxel among the first image voxels based on the constraint map.

* * * * *